United States Patent [19]
Santana

[11] Patent Number: 5,312,322
[45] Date of Patent: May 17, 1994

[54] THREE POINT EXTENSION SPLINT TO TREAT FLEXION CONTRACTURES ABOUT LIMB SYNOVIAL HINGE JOINTS

[75] Inventor: Joseph M. Santana, Ramona, Calif.

[73] Assignee: The United States of America as represented by The Secretary of the Navy, Washington, D.C.

[21] Appl. No.: 970,312

[22] Filed: Nov. 2, 1992

[51] Int. Cl.$^5$ ............................................... A61F 5/00
[52] U.S. Cl. ......................................... 602/20; 602/26
[58] Field of Search ............... 128/877, 878, 881, 892; 602/5, 6, 12, 15, 16, 20, 21

[56] References Cited

U.S. PATENT DOCUMENTS

| | | | |
|---|---|---|---|
| 1,066,190 | 7/1913 | Ellingsworth | 602/5 |
| 1,257,297 | 2/1918 | Brown | 602/16 |
| 1,630,108 | 5/1927 | Buckowitz | 602/5 |
| 2,661,000 | 12/1953 | Gazeley | 602/16 |
| 4,180,870 | 1/1980 | Radulovic | 602/20 |
| 4,417,569 | 11/1983 | Brudny | 602/20 |
| 4,612,919 | 9/1992 | Best . | |
| 4,665,905 | 5/1987 | Brown | 602/16 |
| 4,724,827 | 2/1988 | Schenck . | |
| 5,036,837 | 8/1991 | Mitchell et al. . | |
| 5,117,814 | 6/1992 | Luttrell | 602/16 |
| 5,152,203 | 10/1992 | Fareed | 602/62 |

OTHER PUBLICATIONS

"Corpsman invents new elbow splint"; The Journal, vol. 4, No. 12, Mar. 26, 1992, p. 1.
"Innovative Splint Reduces Elbow Dysfunction"; Advance, Aug. 31, 1992; p. 42.

Primary Examiner—Michael A. Brown
Attorney, Agent, or Firm—A. David Spevack; William C. Garvert

[57] ABSTRACT

A three point extension splint device for correcting flexion contractures about limb synovial hinge joints. The splint device comprises a proximal contact means for contacting the proximal portion of an extremity above the flexion crease of a synovial joint and a distal contact means for contacting the distal portion of an extremity below the flexion crease of a synovial hinge joint. A springy, resilient bridge joins the proximal and distal extremity contact means. These three parts form a anterior assembly. A cupping means that forms the posterior assembly protects the bony prominence of the joint. An adjustable, releasable, strapping means joins the springy, resilient bridge to the cupping means to produce a downward, and centrifugal force in both extremity contact means proportionate to the amount of force exerted by the strapping means thereby causing a myofascial release by the longitudinal stretch of the major muscle and tendon extensions parallel to the long axis of the limb toward the synovial hinge joint while the superficial tissues are stretched in the opposite direction.

12 Claims, 2 Drawing Sheets

THREE POINT EXTENSION SPLINT TO TREAT FLEXION CONTRACTURES ABOUT LIMB SYNOVIAL HINGE JOINTS

BACKGROUND OF THE INVENTION

1. Field of the Invention

This invention relates to an extension splint that lengthens the muscle and soft tissue about an extremity or limb synovial hinge joint to assist in rehabilitating flexion contractures caused by soft tissue injury. More particularly, the invention relates to a three point extension splint to treat flexion contractures about the knee, elbow and/or finger.

2. Description of the Prior Art

Joint contractures are a common complication following fractures, dislocations, and soft tissue injuries about the synovial joints such as the elbow and knee. Perry noted in Prescription Principles, *American Academy of Orthopaedic Surgeons: Atlas of Orthotics*; Biomechanical Principles & Applications, pp 120–122, St. Louis, C. V. Mosby, 1975 that, "restoration of full elbow extension is a strong challenge," and that, "recovery of lost arcs of motion with an orthosis is difficult."

Kottke et al. in The Rationale for Prolonged Stretching for Correction of Shortening of Connective Tissue; *Arch. Phys. Med. Rehabil.*, 47, pp. 345–352, 1966 suggested that prolonged stretching at moderate tension resulted in a significantly increased range of motion about a joint over that achieved by intense short duration stretching. In summary, Kottke stated that, > mobility of loose or areolar connective tissue is related to its structural organization as a meshwork of fibers. The range of mobility depends on the distance between the points of attachment of the collagen fibers. In dense connective tissue, that has little mobility, the fiber meshwork has smaller interstices than those in loose connective tissue with considerable freedom of motion. Normal connective tissue develops a tensile force, that causes a slow, progressive shortening of that connective tissue until stopped by an opposing force. This property of progressive shortening is responsible for the contractures, that develop in soft tissues around joints when motion is limited or prevented. The attachments between collagen fibers show high resistance to suddenly applied tension but relax or creep when exposed to prolonged tension. Utilizing this plastic characteristic of connective tissue, methods have been developed for hip flexors, knee flexors, and ankle plantar flexors. Significantly greater restoration of the motion of these has been obtained, within the limits of pain and without evidence of tearing of tissues, by prolonged stretching at moderate tension than by intense stretching of short duration.

The original treatment to create the prolonged stretching at moderate intensity was to apply a succession of casts where each cast was fixed in a greater angle until the joint was straight. At best, this was inconvenient to body maintenance such as washing. At worst, it took months of incapacitation and lead to a deterioration of other muscle groups.

Others have designed devices to replace the cast method. These devices are all based on some variation of a three point extension. Best, in U.S. Pat. No. 4,612,919 issued Sep. 23, 1986, describes an adjustable limb support designed to provide this slow stretching with some control in the hands of the patient. The Best device has a rigid metal frame work that appears to be heavy, cumbersome and does not appear to contemplate or provide for the use of variable pressure intensities during the course of the day. Also, Best does not provide easy adjustment to the patient or a device that is secure and safe to both patient and sleeping companion if the device is worn while sleeping.

Brown, in U.S. Pat. No. 4,665,905 issued May 19, 1987, describes a lighter weight, wire frame dynamic elbow and knee extension brace. The Brown brace appears to have an adjustable length, but not an adjustment for the tension created by the spring arrangement.

Green et al., describes a turnbuckle orthotic correction device in *J. Bone and Joint Surgery*, Vol 61-A, No. 7, pp 1092–1095, October 1979. B. C. Parker describes another variation of a dynamic elbow extension splint in *American J. Occupational Therapy*, Vol. 41, No. 12, pp 825–826, December 1987. Yet another variation of a gear controlled dynamic extension splint is taught by Mitchell in U.S. Pat. No. 5,036,837 issued Aug. 6, 1991. A dynamic traction device for the finger is illustrated by Schenck in U.S. Pat. No. 4,724,827 issued Feb. 16, 1988. These devices do not provide a light weight easily adjustable dynamic extension splint that can provide myofascial release.

SUMMARY OF THE INVENTION

Accordingly, an object of this invention is a device that provides a myofascial release about a synovial hinge joint.

Another object of the invention is a splint that produces parallel forces between the muscles and tendons with opposing forces of the epidermis and the dermis thus creating a myofascial release.

Yet an additional object of this invention is a device that can easily be adjusted by the patient to allow maximum patient tolerance through a self-administered "home" exercise program.

A further object of this invention is a device that allows different intensities of exercise to be performed quickly by the patient to comply with a daily regime of physical therapeutic exercise.

Yet another object of this invention is a device with a low profile that permits the unobtrusive wearing of the device for exercise regime while carrying on other unrelated activities.

Another object of this invention is a device that can be selectively worn by the patient thereby permitting unencumbered body maintenance including body cleaning and muscle toning of other body and arm flexion.

These and additional objects of the invention are accomplished by a three point extension splint device for correcting flexion contractures about limb synovial hinge joints. The splint device comprises a proximal contact means for contacting the proximal portion of an extremity above the flexion crease of a synovial joint and a distal contact means for contacting the distal portion of an extremity below the flexion crease of a synovial hinge joint. Proximal means the portion of an extremity closer to the torso and distal means the portion of the extremity further away from the torso. A springy, resilient bridge joins the proximal and distal extremity contact means. These three parts form a anterior assembly. A cupping means that forms the posterior assembly protects the bony prominence of the joint. The cupping means is arranged so that it protects and does not damage the joint. An adjustable, releasable, strapping means joins the springy, resilient bridge to the cupping means to produce a downward, and centrifugal force in both extremity contact means proportionate to the amount of force exerted by the strapping means thereby causing a myofascial release by the longitudinal stretch of the major muscle and tendon extensions parallel to the long axis of the limb toward the synovial hinge joint while the superficial tissues are stretched in the opposite direction.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
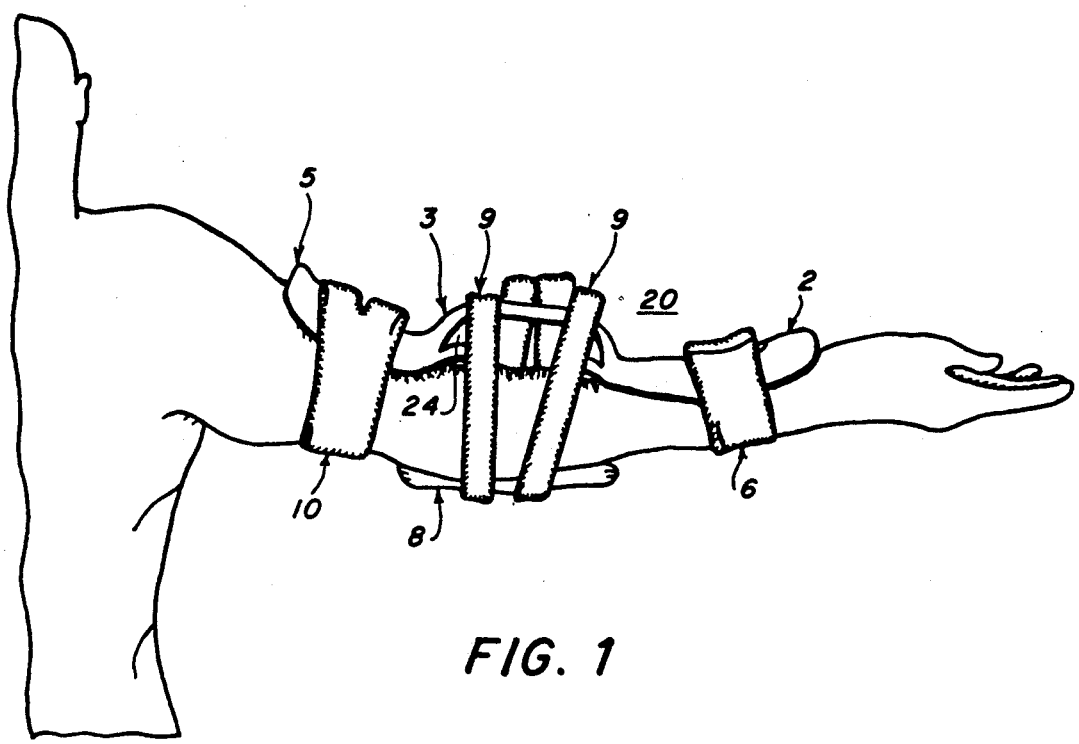
FIG. 1 is a rear view of a patient wearing the splint device in an extended position.

The three point extension splint device for correcting flexion contractures about limb synovial hinge joints of this invention provides longitudinal stretch of the major muscle and tendon extensions parallel to the long axis of the extremity while the superficial tissues are stretched in the reverse direction thus creating a myofascial release. Although the splint device is principally designed to treat the elbow or knee, the splint device will work equally well with any finger joint where the joint can be fitted with the contact means and cupping means. In principle, as illustrated in application to an arm, the splint device comprises a proximal contact means for contacting the proximal portion of the arm above the fold of a synovial hinge joint and a distal contact means for contacting the fore arm below the fold of the synovial hinge joint. The fold is the inner part of the joint. A springy, resilient bridge joins the proximal and distal contact means. In the preferred embodiment, the contact means and the bridging means are formed out of one piece of thermoplastic material commonly used in occupational therapy and orthopedics to splint patients. The contact means are formed into saddles and padded as is usually done in good orthopedic practice. The bridge is made springy by causing it to be formed into what is designated for this application as a U shape. Actually the shape is more in the form of the Greek letter omega ($\Omega$) so a downward force on the apex of the curve would cause the legs of the bridge to splay out, transmitting some of the force parallel to the limb and some of the force perpendicular to the limb. "Springy" means that a downward pressure on the bridge will cause force to be transmitted downward and outward to each of the contacts and the bridge will reassume its shape when the downward force is removed. Alternatively, the contact means can be separate pieces made out of materials commonly used or adaptable for use in orthopedic treatment and therapy. The bridge can be formed from material that has "spring" such as steel, plastics, composite materials such as carbon composites or similar materials. The bridge must be capable of transmitting the force vectors required to accomplish the objects of this invention. A securing or holding means, such as securing straps are preferably provided at the end of each contact to help in holding the anterior assembly to the arm. These securing straps do not contribute to the treatment mechanism of splint.

A cupping means protects the bony prominence of the synovial hinge joint. The cupping means is arranged so that it protects and does not damage the joint. The exact shape of the cupping means is different for each particular joint for reasons well known in this area. The cup for an elbow or knuckle can be formed from thermoplastic material or other material shaped to accommodate the bone. Holes in the cup are provided to accommodate the bony prominence. The cup for a knee joint must accommodate the "floating" knee cap. The cup serves as one pressure control points in the mechanism to exert a downward force on the bridge. The cup must accept continued maximum pressure during the maximum pressure treatment period that is set as close as possible to the patient's tolerance point for that treatment while causing no injury or pain to the patient. Alternatively, the cup can be formed of net, cloth, or solid materials as long as the material can protect the joint and withstand the forces exerted on the cup.

An adjustable, releasable, force producing strapping means joins the springy, resilient bridge to the cupping means to produce a downward, and outward force in both limb contact means dependant on the amount of force exerted by the strapping means thereby causing a myofascial release by the longitudinal stretch of the major muscles and tendons parallel to the long axis of the limb while the superficial tissues are stretched in the reverse parallel direction. In the preferred embodiment, the straps are elastic material with at least one face covered by one of the complementary VELCRO® pair. VELCRO® is a nylon material made with both a surface of tiny hooks and complementary surface of a clinging pile. The straps function to "pull down" the upper bridge and contacts transmitting force to the limb to straighten the joint. In alternative embodiments, these straps can be non-elastic straps that rely on the elasticity of the bridge to transmit force and provide flexibility. Alternatively, the straps can be bands of rubber or steel springs attached to protuberances on the cup and bridge. Preferably the strap has some flexibility and elasticity. The degree of elasticity or force exerted by the straps is subjective within the skill of the occupational therapist or technician. As explained below, the maximum force to be exerted by the straps is not to exceed patient's tolerance. The reduce tension should be a reduction to between 15% to 30% of the maximum force, preferably about 25% of the maximum force. Of course, this can be varied by the judgement of the practitioner dependant on the patients progress.

An embodiment of the invention is illustrated in FIG. 1 attached to a patient's arm. In FIG. 1, an anterior assembly 20 is made of one piece of a resilient thermoplastic material formed into a proximal contact 5 and a distal contact 2 joined by a resilient, springy bridge 3. The bridge is formed into a U shape 24 to provide the springy property. Force producing elastic straps 9 join the posterior assembly in the form of an elbow cup 8 to the bridge 3. The tightness with which the straps are drawn controls the amount of force exerted on the bridge. Marks on the straps can designate minimum and maximum force for the patient's self treatment.

Figure 2:
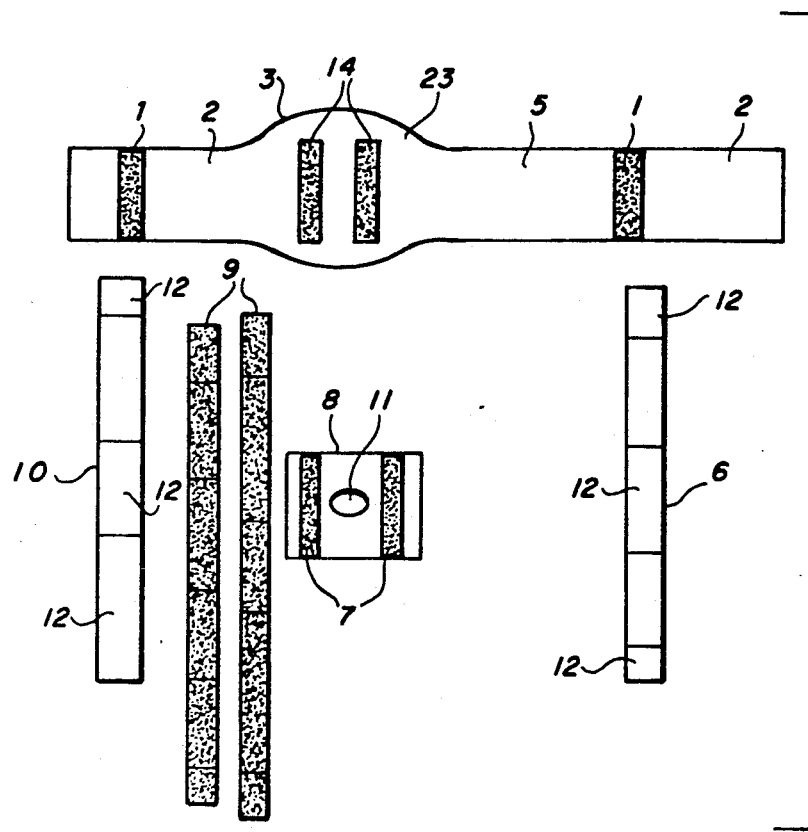
FIG. 2 is a plan view of the parts that constitute one embodiment of the invention.

Securing straps 6 and 10 help to hold the anterior assembly to the limb. As seen in FIG. 2, hook VELCRO® strips 1 on contacts 2 and 5 cooperate with complementary VELCRO® strips 12 to hold the anterior assembly.

The elbow cup 8 is provided with an olecranon window 11 to accommodate the bone. In this embodiment, the cup is formed from thermoplastic, padded, and provided with VELCRO® strips 7 that cooperate with VELCRO® strips 9 through complementary VELCRO® strips 4 to exert force on bridge 3. The amount of force varies with the tightness of the strap 9 and the elasticity of strap 9. Straps of different elastic strength are used at different times in the course of therapy dependant on the condition and needs of the patient. The same elastic variation can be used with spring alternatives to elastic VELCRO® covered strips. In the usual treatment with this device, the therapist sets the device with the straps at maximum tension. The patient is instructed to use this setting, either with a therapist present, or in a home program without a therapist, three or four times a day for about one hour for each exercise session. The splint does not have to be worn during non-exercise periods. At night, the patient wears the device at the reduce tension designated by the therapist. Of course, the treatment regime can be varied by the professional judgement of the therapist.

Figure 3:
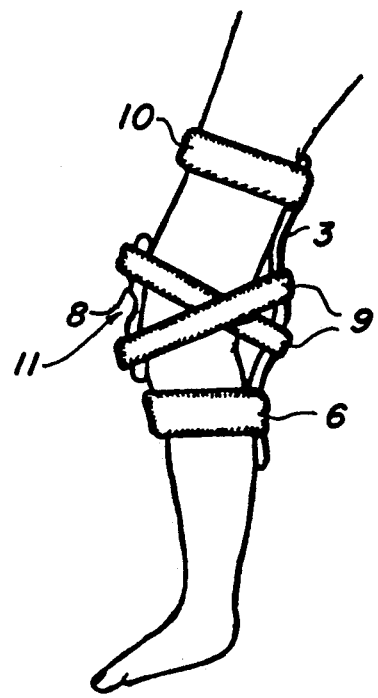
FIG. 3 is an embodiment of the invention applied to a knee.
Figure 4:
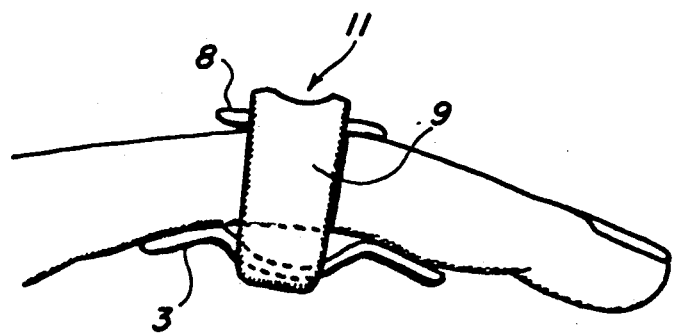
FIG. 4 is an embodiment of the invention applied to a finger.

FIGS. 3 and 4 show embodiments of the invention applied to a knee and finger respectively. The parts of the embodiment are the same as described for FIGS. 1 and 2 and are identified by the same numeral indicators. The size of each part will vary dependant on its specific application.

Having described the invention, the following examples are given to illustrate specific applications of the invention including the best mode now known to perform the invention. These specific examples are not intended to limit the scope of the invention described in this application.

FABRICATION TECHNIQUES

MATERIALS:
1. Any low heat thermoplastic.
2. 2" VELFOAM ... length as indicated (required by particular patient) for proximal and distal splint straps.
3. 1" NEOLOOP strapping as indicated to accommodate the elbow.
4. Adhesive backed VELCRO® hook.
5. Padding as indicated for patient comfort.
6. Any VHS cassette box.

PATTERN:
PART 1 (ANTERIOR ASSEMBLY 20)=2½ times the width of the arm by the distance from the proximal ⅓ of the arm to the distal ⅔ of the forearm.
PART 2 (POSTERIOR ASSEMBLY 8)=8" by 4".

FABRICATION:
Part 1:
The patient lies in the supine position with the affected arm slightly abducted at the shoulder and the elbow extended as much as allowable within the patient's tolerance. Fold PART 1 in half lengthwise to increase the strength of the splint. Cut the edges of the splint to form a smooth comfortable finish. Place an object, such as a VHS cassette box, widthwise and centered along the elbow flexion crease. Mold PART 1 to the patient's arm and forearm. When removed, the VHS cassette box will leave a 1" raised area in the center of PART 1 over the elbow flexion crease.

Part 2:
Fold PART 2 in half, and cut the edges to form a smooth comfortable finish. Mold PART 2 to the patient's elbow using the OLECRANON PROCESS as the center point. Pad PART 2 and create a window for the OLECRANON PROCESS as this area is prone to pressure sores.

Secure PART 1 with velfoam at the arm and the forearm as shown in FIG. 1. Place the adhesive back VELCRO® hook 7 to the myofascial bridge 3 of PART 1 and the posterior portion of PART 2. Once secured with neoloop, this area is where the patient is able to adjust the tension to the desired amount.

APPLICATION:
HIGH INTENSITY STRETCHING four times daily for one hour.
LOW INTENSITY STRETCHING for overnight use.

CASE STUDIES:

| Case: | 1 | 2 | 3 |
|---|---|---|---|
| Age/Sex: | 22/M | 23/M | 52/F |
| Diagnoses: | ORIF of L Proximal Radial Head Fx | Avulsion Injury to R Elbow | L Ulnar Head Fx |
| Time Since Injury: | 4 Months | 7 Months | 4 Months |
| Before Splinting Ext/Flex: | −24/128 | −28/140 | −24/138 |
| After Splinting Ext/Flex: | −10/130 | −12/140 | −8/142 |
| Time in Splint (Days): | 12 | 13 | 6 |

ORIF = Open Reduction Internal Fixation; Fx = Fracture; L = Left; R = Right

RESULTS USING 0-145 AS THE NORM FOR TOTAL ACTIVE MOTION (TAM):

| Case: | 1 | 2 | 3 |
|---|---|---|---|
| TAM Before Splint: | 72% | 77% | 79% |
| TAM After Splint: | 83% | 88% | 92% |
| Percent Gained Post Splint Wear: | 11% | 11% | 13% |

DISCUSSION:
All three cases had a significant increase in total active motion (TAM) in a short period of time. All three cases maintained and/or increased their active flexion. The SPLINT is a low profile splint that is effective in managing contractures of the elbow. The patient has full control of the amount of tension he or she applies to their arm, therefore the patient will never have tension beyond their tolerance.

Obviously, many modifications and variations of the present invention are possible in light of the above teachings. It is therefore to be understood that, within the scope of the appended claims, the invention may be practiced otherwise than as specifically described.

What is claimed:
1. A device for correcting flexion contractures about synovial hinge joints of an extremity comprising:
    a proximal contact means for contacting the proximal portion of an extremity above the flexion crease of a synovial joint, a distal contact means for contacting the distal portion of an extremity below the flexion crease of a synovial joint, a springy, resilient bridge joining the proximal and distal extremity contact means forming an anterior assembly, a posterior assembly cupping means to protect the bony prominence of the synovial joint, and an adjustable, releasable, strapping means joining the springy, resilient bridge to the cupping means to produce a downward, and outward force in the proximal contact means and distal contact means dependant on the amount of force exerted by the strapping means thereby causing a myofascial release by stretching the major muscles and tendons parallel to the long axis of the limb while the superficial tissues are stretched in the opposite direction by contact with the proximal and distal contact means.

2. A device according to claim 1 wherein the proximal and distal extremity contacts have a releasable strap to assist in holding the anterior assembly to the extremity.

3. A device according to claim 2 wherein the synovial joint is the elbow.

4. A device according to claim 3 wherein the adjustable, releasable strapping means is formed of elastic self gripping strap material and the cupping means and resilient bridge each have a gripping zone to mate with the gripping strap material.

5. A device according to claim 4 wherein the proximal and distal extremity contacts and the bridge are all formed of one piece of thermoplastic material 2½ times the width of the arm by the distance from the proximal ⅓ of the arm to the distal ⅓ of the forearm and the bridge is in the form of a U.

6. A device according to claim 2 wherein the proximal and distal extremity contacts and the bridge are all formed of one piece of thermoplastic material 2½ times the width of the extremity by the distance from the proximal ⅓ of the upper extremity to the distal ⅔ of the lower extremity and the bridge is in the form of a U.

7. A device according to claim 2 wherein the synovial joint is the knee.

8. A device according to claim 7 wherein the adjustable, releasable strapping means is formed of elastic self gripping strap material and the cupping means and resilient bridge each have a gripping zone to mate with the gripping strap material.

9. A device according to claim 8 wherein the proximal and distal leg contacts and the bridge are all formed of one piece of thermoplastic material 2½ width of the leg by the distance from the proximal ⅓ of the upper leg to the distal ⅔ of the lower leg and the bridge is in the form of a U.

10. A device according to claim 7 wherein the proximal and distal leg contacts and the bridge are all formed of one piece of thermoplastic material and the bridge is in the form of a U.

11. A device according to claim 2 wherein the synovial joint is in the finger.

12. A device according to claim 1 wherein the proximal and distal extremity contacts and the bridge are all formed of one piece of thermoplastic material 2½ times the width of the extremity by the distance from the proximal ⅓ of the upper extremity to the distal ⅔ of the lower extremity and the bridge is in the form of a U.

* * * * *